United States Patent
Liu et al.

(10) Patent No.: US 10,618,940 B2
(45) Date of Patent: Apr. 14, 2020

(54) METHOD FOR RECONSTRUCTING ASPERGILLUS NIGER TO INCREASE CITRATE PRODUCTION

(71) Applicants: Jiangnan University, Wuxi (CN); JIANGSU GUOXIN UNION ENERGY CO LTD, Wuxi (CN)

(72) Inventors: Long Liu, Wuxi (CN); Jian Chen, Wuxi (CN); Guocheng Du, Wuxi (CN); Jianghua Li, Wuxi (CN); Xian Yin, Wuxi (CN); Zhijie Hu, Wuxi (CN); Jianwei Jiang, Wuxi (CN); Fuxin Sun, Wuxi (CN); Sai Jin, Wuxi (CN); Cheng Zhang, Wuxi (CN); Xiaodong Jiang, Wuxi (CN)

(73) Assignee: Jiangnan University, Wuxi (CN)

( * ) Notice: Subject to any disclaimer, the term of this patent is extended or adjusted under 35 U.S.C. 154(b) by 37 days.

(21) Appl. No.: 15/868,136

(22) Filed: Jan. 11, 2018

(65) Prior Publication Data
US 2018/0194814 A1  Jul. 12, 2018

(30) Foreign Application Priority Data

Jan. 12, 2017 (CN) .......................... 2017 1 0022533

(51) Int. Cl.
| | | |
|---|---|---|
| C07K 14/38 | (2006.01) | |
| C12N 15/80 | (2006.01) | |
| C12N 15/52 | (2006.01) | |
| C07K 14/37 | (2006.01) | |
| C12P 7/62 | (2006.01) | |
| C12P 7/48 | (2006.01) | |

(52) U.S. Cl.
CPC .............. C07K 14/38 (2013.01); C12N 15/80 (2013.01); C12P 7/48 (2013.01); C12P 7/625 (2013.01)

(58) Field of Classification Search
None
See application file for complete search history.

(56) References Cited

PUBLICATIONS

Show et al. Overview of citric acid production from Aspergillus niger. Published online Apr. 20, 2015. Frontiers in Life Science. vol. 8, No. 3, p. 271-283. (Year: 2015).*

* cited by examiner

Primary Examiner — Channing S Mahatan
(74) Attorney, Agent, or Firm — IPro, PLLC

(57) ABSTRACT

The invention discloses a method for increasing citrate production from genome reconstructed *Aspergillus niger*. The method is to insert a gene of low affinity glucose transporter, LGT1, to genome of *A. niger*. The expression level of LGT1 is under control of promoter Pgas. The genome reconstructed *A. niger* is tolerant to higher fermentation temperature and lower pH than that of the parental strain. Moreover, the production, yield and purity of product from reconstructed *A. niger* are higher than that of parental strain, and the fermentation time is shorter.

20 Claims, No Drawings
Specification includes a Sequence Listing.

METHOD FOR RECONSTRUCTING ASPERGILLUS NIGER TO INCREASE CITRATE PRODUCTION

TECHNICAL FIELD

The disclosure herein relates to the field of bioengineering technology, and more particularly to increase citrate production by genome reconstruction of *A. niger*.

BACKGROUND

Citrate is a kind of organic acid with largest production annually around 1.7 billion tons and the demand is increasing for 3.5-4.0% each year. China is the largest producer and top exporter of citrate, and 53% of the citrate production annually is from China. Many study aimed to improve the production process of citrate fermentation. As the basis of fermentation, industrial strain improvement is also a focus of study. During citrate fermentation, *A. niger* absorbs glucose as carbohydrate resource. Torres examined that 2 Km existed during glucose absorption by *A. niger*, which were 260 μM and 3.67 mM, suggesting both high affinity and low affinity glucose transport system worked in *A. niger*. Furthermore, the low affinity glucose transport system provided the metabolite during citrate fermentation. Nevertheless, the system only worked when glucose concentration was above 50 g·L$^{-1}$. Glucose transportation is the first step of citrate fermentation, and glucose transportation system is crucial for citrate production, thus adjust the glucose transport system may enhance citrate production.

SUMMARY

To solve the technology problem analyzed above, the invention provides a method for increasing citrate production from genome reconstructed *A. niger*. The genome reconstructed *A. niger* is tolerant to higher fermentation temperature and lower pH than that of the parental strain. Moreover, the production, yield and purity of product from reconstructed *A. niger* are higher than that of parental strain, and the fermentation time is shorter.

In an embodiment, the genome of reconstructed *A. niger* with higher citrate production is inserted with a low affinity glucose transporter, LGT1, which is under control of Pgas.

In an embodiment, the gene sequence of LGT1 is shown in SEQ ID NO.1, with its amino acid sequence shown in SEQ ID NO.2.

In an embodiment, the Pgas promoter controlling the expression level of LGT1 is a low pH inducible promoter, and the promoter sequence is shown in SEQ ID NO.3.

In an embodiment, the expression cassette of LGT1 contains promoter of Pgas, LGT1 gene and terminater of trp in order of Pgas-LGT1-trp.

In an embodiment, the sequence of Pgas is shown in SEQ ID NO.3, the amino acid sequence of LGT1 is shown in SEQ ID NO.2, and the sequence of trp ternimater is shown in SEQ ID NO.6.

In an embodiment, the reconstruction method of *A. niger* contains the following steps:
(1) Construction of expression cassette of LGT1 with Pgas-LGT1-trp;
(2) Construction of resistant gene expression cassette gpdA-hph-trp;
(3) Transportation of expression cassette in step (1) and (2) into *A. niger*, screening of resistant strains and confirming reconstructed strains with PCR.

In an embodiment, the sequence of gpdA promoter in resistant gene cassette is shown in SEQ ID NO. 4.

In an embodiment, the sequence of resistant gene, hph, in resistant gene cassette is shown in SEQ ID NO. 5.

By means of the above technical solutions, the invention has the following advantages:

The invention uses low pH inducible promoter to promote expression of LGT1 in *A. niger*, as a result enhanced glucose absorption during acid producing period and finally enhanced citrate production. The parental strain used is *A. niger* H915-1. The citrate production of reconstructed strain improved for 6.5%. The production increased for 40.3% when fermentation at 42° C., and fermentation time reduced for 10 h. With lower pH media, the production increased for 6.9%.

DETAILED DESCRIPTION

Example 1

RNA Extraction from *A. niger*

Conidia of *A. niger* (1×10$^6$) were inoculated in 100 mL citrate fermentation medium (a mixture of corn steep liquor and corn starch with a total sugar content of 16% and total nitrogen content of 0.08%) at 35° C. and 250 r/min for 48 h. The mycelia were harvested with Miracloth (Calbiochem, San Diego, Calif., USA), washed with sterile water and frozen in liquid nitrogen. Tissues were ground by Liquid nitrogen grinding, and the total RNA of *A. niger* was isolated with a RNeasy Plant Mini Kit (QIAGEN, Germantown, Md., USA). The RNA was transcripted into cDNA using PrimeScript RT reagent Kit with gDNA Eraser (Takara, Dalian, China).

Example 2

Genome Extraction from *A. niger*

Conidia of *A. niger* were inoculated in malt extract liquid medium (3% malt extract and 0.5% tryptone) at 35° C. and 250 r/min for 48 h. The mycelia were harvested with Miracloth (Calbiochem, San Diego, Calif., USA), washed with sterile water and frozen in liquid nitrogen. Tissues were ground by Liquid nitrogen grinding, and the genome of *A. niger* was isolated with a DNeasy Plant Mini Kit (QIAGEN, Germantown, Md., USA).

Example 3

Construction of LGT1 Expression Cassette

The trp terminator is amplified with primer trp-F (sequence shown in SEQ ID NO. 7) and trp-R (sequence shown in SEQ ID NO.8) using pAN7-1 as template, and added the restriction sites of Pst I and Hin dIII at the 5' and 3' ends. The sequence is connected to pMD19 and sequenced. Then, the sequence was digested by Pst I and Hin dIII and connected to pUC19 to obtain pUC19-trp.

The Pgas promoter (sequence shown in SEQ ID NO. 3) is amplified with primer Pgas-F (sequence shown in SEQ ID NO. 9) and Pgas-R (sequence shown in SEQ ID NO.10) using *A. niger* genome as template with restriction sites of Eco RI and Kpn I at the 5' and 3' ends. Then, the sequence was digested by Eco RI and Kpn I and connected to pUC19-trp to obtain pUC-Pgas-trp.

The LGT1 CDS (sequence shown in SEQ ID NO. 1, and amino acid sequence shown in SEQ ID NO. 2) is amplified with primer Pgas-LGT1-F (sequence shown in SEQ ID NO. 11) and Trp-LGT1-R (sequence shown in SEQ ID NO.12)

using *A. niger* cDNA as template with 20 bp homologous sequence of pUC-Pgas-trp at the 5' and 3' ends. Then, the sequence was connected to pUC-Pgas-trp using Vazyme One Step Clone Kit (Vazyme, Nanjing, China) to obtain pGTH with gas-LGT1-trp cassette.

The primer used are as follows:

```
trp-F:
ctgcagGATCCACTTAAACGTTACTGAAATC trp-R:
aagcttCTCGAGTGGAGATGTGGAGTGG

Pgas-F:
gaattcCTGCTCTCTCTCTGCTCTCTTTCT

Pgas-R:
ggtaccGTGAGGAGGTGAACGAAAGAAGAC

Gas-LGT1-F:
gttcacctcctcacGGTACCATGGGTGTCTCTAATATGATGTC

Trp-LGT1-R:
TAACGTTTAAGTGGATCGGATCCTTACTCGCGGAGCTCAGTGG
```

Example 4

Preparation and Transformation of Protoplast of *A. niger*

Conidia (3×10⁵/mL) were inoculated in PDA medium over night at 200 r/min under 30° C. The mycelium was harvested via filtration through Miracloth and washed with sterile water.

Protoplastation was achieved by digesting 0.5 g mycelium in KMC with 0.5 g/L lysing enzymes for 3 h at 100 rpm under 37° C. The protoplasts were filtered through Miracloth and collected via centrifugation at 1,000 rpm under 4° C. for 10 min and subsequently washed twice with the same volume STC, and finally resuspended in 100 μL STC and directly used for transformation.

Ten micrograms of expression cassette was mixed with 100 μL protoplasts and 330 μL polyethylene glycol (PEG) solution and kept on ice for 20 min. After mixing with an additional 2 mL PEG solution and incubating at room temperature for 10 min, the protoplast mixture was diluted with 4 mL STC. The aliquots were mixed with 4 mL liquid top agar warmed to 48° C., spread on bottom agar containing 180 mg/L hygromycin, and incubated at 35° C. for 4-7 days until clones appeared. All transformants were purified three times via single-colony isolation on the selection medium.

Example 5

Conidia of *A. niger* were inoculated in malt extract liquid medium (3% malt extract and 0.5% tryptone) at 35° C. and 250 r/min for 48 h. The mycelia were harvested with Miracloth (Calbiochem, San Diego, Calif., USA), washed with sterile water and frozen in liquid nitrogen. Tissues were ground by Liquid nitrogen grinding, and the genome of *A. niger* was isolated with a DNeasy Plant Mini Kit (QIAGEN, Germantown, Md., USA). The correct integration was verified with PCR analysis by using primers of Gas-LGT1-F and Trp-LGT1-R with genome as template.

The Control Samples

Control Example 1

The hph expression cassette, which contains PgpdA (sequence shown in SEQ ID NO. 4), hph (sequence shown in SEQ ID NO. 5) and trp terminator (sequence shown in SEQ ID NO. 6), is amplified with primer gpd-F (sequence shown in SEQ ID NO. 13) and Ttrp-R-2 (sequence shown in SEQ ID NO.14) using pAN7-1 (genbank No. Z32698.1) as template.

```
gpd-F:
CAATTCCCTTGTATCTCTACACACAG

Ttrp-R-2:
CTCGAGTGGAGATGTGGAGTGG
```

Control Example 2

Preparation and Transformation of Protoplast of *A. niger*

Conidia (3×10⁵/mL) were inoculated in PDA medium over night at 200 r/min under 30° C. The mycelium was harvested via filtration through Miracloth and washed with sterile water.

Protoplastation was achieved by digesting 0.5 g mycelium in KMC with 0.5 g/L lysing enzymes for 3 h at 100 rpm under 37° C. The protoplasts were filtered through Miracloth and collected via centrifugation at 1,000 rpm under 4° C. for 10 min and subsequently washed twice with the same volume STC, and finally resuspended in 100 μL STC and directly used for transformation.

Ten micrograms of expression cassette was mixed with 100 μL protoplasts and 330 μL polyethylene glycol (PEG) solution and kept on ice for 20 min. After mixing with an additional 2 mL PEG solution and incubating at room temperature for 10 min, the protoplast mixture was diluted with 4 mL STC. The aliquots were mixed with 4 mL liquid top agar warmed to 48° C., spread on bottom agar containing 180 mg/L hygromycin, and incubated at 35° C. for 4-7 days until clones appeared. All transformants were purified three times via single-colony isolation on the selection medium.

The Test

Four strains of *A. niger*, which are obtained as test sample and control sample, *A. niger* Co82 and *A. niger* TN-A09, were incubated in ME medium (3% malt extract and 0.5% tryptone) and kept at 35° C. for 7 days. Conidia were harvested and inoculated into seed medium (corn starch medium with total sugar concentration at 10% and total nitrogen at 0.2%) and cultured at 37° C. 250 rpm for 24 h. Then the seed culture was inoculated into fermentation medium with 1/10 volume. The citrate fermentation was lasted for 72 h at 35° C. 250 rpm. The sample was centrifuged, after the mycelium were discarded, the liquid was diluted for 10 times and tested citrate concentration by HPLC. The test result was shown in table 1.

TABLE 1

|  | Citrate (g/100 mL) | Yield (%) | Fermentation time (h) |
| --- | --- | --- | --- |
| Test sample | 18.2 | 98 | 55 |
| Control sample | 13.4 | 92 | 60 |
| *A. niger* Co82 | 13 | 92 | 60 |
| *A. niger* TN-A09 | 12.5 | 92 | 60 |

Citrate concentration was detected by Agilent 1200 (containing UV detector, refractive index detector and workstation); HPLC condition: HPX87 H column (4.6×250 mm, 5 μm), mobile phase of 5 mM $H_2SO_4$, flow velocity of 0.6 mL/min, sample size of 10 μL, column temperature at 30° C. and detect with UV at 210 nm.

The result showed that the citrate production and yield of test sample were higher than that of other strains in submerged aerobic fermentation.

Threer strains of *A. niger*, which are obtained as test sample and control sample, and *A. niger* zjs-8, were incubated in ME medium (3% malt extract and 0.5% tryptone) and kept at 35° C. for 7 days. Conidia were harvested and inoculated into seed medium (corn starch medium with total sugar concentration at 10% and total nitrogen at 0.2%) for $10^6$/mL and cultured at 37° C. 250 rpm for 24 h. Then the seed culture was inoculated into fermentation medium with 1/10 volume. The citrate fermentation was lasted for 72 h at 42° C. 250 rpm. The sample was centrifuged, after the mycelium were discarded, the liquid was diluted for 10 times and tested citrate concentration by HPLC. The test result was shown in table 2.

TABLE 2

|  | Citrate (g/100 mL) | Yield (%) | Fermentation time (h) |
|---|---|---|---|
| Test sample | 17.9 | 94 | 60 |
| Control sample | 10.7 | 66.8 | 70 |
| *A. niger* zjs-8 | 10 | 61.83 | 60 |

The result showed that the test sample was more tolerant to high temperature and citrate production and yield were higher than *A. niger* zjs-8 under 42° C.

Three strains of *A. niger*, which are obtained as test sample and control sample and *A. niger* Co82, were incubated in ME medium (3% malt extract and 0.5% tryptone) and kept at 35° C. for 7 days. Conidia were harvested and inoculated into seed medium (corn starch medium with total sugar concentration at 10% and total nitrogen at 0.2%, pH 3.5) and cultured at 37° C. 250 rpm for 24 h. Then the seed culture was inoculated into fermentation medium (pH 2.0) with 1/10 volume. The citrate fermentation was lasted for 72 h at 42° C. 250 rpm. The sample was centrifuged, after the mycelium were discarded, the liquid was diluted for 10 times and tested citrate concentration by HPLC. The test result was shown in table 3.

TABLE 3

|  | Citrate (g/100 mL) | Yield (%) | Fermentation time (h) |
|---|---|---|---|
| Test sample | 18.9 | 99.5 | 60 |
| Control sample | 14 | 93 | 60 |
| *A. niger* Co82 | 13 | 93 | 65 |

The result showed that the test sample produced citrate with higher production and yield in shorter fermentation time in acid condition. The test sample was more tolerant to acid.

What is claimed is:

1. A recombinant *Aspergillus niger* strain, comprising:
a genome comprising an inserted low affinity glucose transporter gene LGT1, wherein the glucose transporter gene LGT1 transporter is under the control of a Pgas promoter,
wherein the glucose transporter gene LGT1 sequence is SEQ ID NO:1,
wherein the Pgas promoter sequence is SEQ ID NO:3, and
wherein the *A. niger* strain produces a higher relative amount of citrate as compared with a wild type *A. niger* strain grown under identical conditions.

2. The recombinant *A. niger* strain according to claim 1, wherein the glucose transporter gene LGT1 encodes a protein having the sequence SEQ ID NO:2.

3. The recombinant *A. niger* strain according to claim 1, wherein the Pgas promoter controlling the expression level of LGT1 is induced by a low pH of between pH 2.0 and pH 3.5.

4. A expression cassette of LGT1 comprising a promoter of Pgas, LGT1 gene and terminator of trp in order of Pgas-LGT1-trp.

5. The expression cassette in claim 4, wherein a sequence of Pgas is set forth in SEQ ID NO:3, an amino acid sequence of LGT1 is set forth in SEQ ID NO:2, and a sequence of trp terminator is set forth in SEQ ID NO:6.

6. The recombinant *Aspergillus niger* strain of claim 1, wherein the gene sequence of glucose transporter gene LGT1 and promoter Pgas are encoded onto an expression cassette transformed into the *A. niger* strain.

7. The recombinant *Aspergillus niger* strain of claim 6, wherein the expression cassette further comprises at least one trp terminator sequence of SEQ ID NO:6.

8. The recombinant *Aspergillus niger* strain of claim 6, wherein the expression cassette further comprises a gpdA promoter sequence of SEQ ID NO:4.

9. The recombinant *Aspergillus niger* strain of claim 6, wherein the expression cassette further comprises a hygromycin resistance (hph) gene sequence of SEQ ID NO:5.

10. The recombinant *Aspergillus niger* strain of claim 6, wherein the expression cassette encodes a trp terminator sequence of SEQ ID NO:6, a gpdA promoter sequence of SEQ ID NO:4, and an hgh gene sequence of SEQ ID NO:5.

11. The recombinant *Aspergillus niger* strain of claim 10, wherein the expression cassette sequences are in the order of gpdA-hph-trp and Pgas-LGT1-trp.

12. The recombinant *Aspergillus niger* strain of claim 1, wherein the *A. niger* strain is derived from *A. niger* strain H915-1.

13. The recombinant *Aspergillus niger* strain of claim 1, wherein the amount of citrate produced by the *A. niger* strain is at least 6.5% higher under identical conditions than a corresponding wild type *Aspergillus niger* strain.

14. The recombinant *Aspergillus niger* strain of claim 1, wherein the amount of citrate produced by the *A. niger* strain is at least 40.3% higher under identical conditions than a corresponding wild type *Aspergillus niger* strain.

15. A method for the reconstruction of reconstructed *A. niger* mentioned in claim 1, comprising the following steps:
(1) constructing an expression cassette of LGT1 with Pgas-LGT1-trp;
(2) Constructing a resistant gene expression cassette gpdA-hph-trp;
(3) inserting expression cassette in step (1) and (2) into *A. niger*, screening resistant strains and confirming reconstructed strains with PCR.

16. The method in claim 15, wherein a sequence of gpdA promoter in resistant gene cassette is set forth in SEQ ID NO: 4.

17. The method in claim 15, wherein a sequence of resistant gene hph in resistant gene cassette is set forth in SEQ ID NO: 5.

18. A method of expressing citric acid from *Aspergillus niger*, which comprises:

incubating an *A. niger* strain in growth medium comprising malt extract and tryptone at 35° C. for seven days to generate conidia, wherein the *A. niger* strain comprises a genome comprising a low affinity glucose transporter gene LGT1, wherein the glucose transporter gene LGT1 transporter is under the control of a Pgas promoter, wherein the glucose transporter gene LGT1 sequence is SEQ ID NO:1, and wherein the Pgas promoter sequence is SEQ ID NO:3, harvesting the conidia, inoculating seed medium with the conidia at a density of $10^6$ per mL to generate a seed culture, wherein the seed medium comprises corn starch medium comprising a total sugar concentration of 10% and a total nitrogen concentration of 0.2%, growing the conidia in the seed medium at 37° C. for 24 hours at pH 3.5, inoculating a fermentation medium with the seed culture at 1/10 volume, incubating the fermentation medium for 72 hours at 42° C. at pH 2.0, centrifuging the fermented fermentation medium and discarding mycelium to obtain citric acid.

19. The method of claim 18, wherein the *A. niger* strain produces a higher relative amount of citrate as compared with a wild type *A. niger* strain grown under identical conditions.

20. The method of claim 18, wherein the *A. niger* strain produces between 6.5% and 40.3% more citrate as compared with a wild type *A. niger* strain under identical conditions.

* * * * *

SEQUENCE LISTING

<160> NUMBER OF SEQ ID NOS: 14

<210> SEQ ID NO 1
<211> LENGTH: 1683
<212> TYPE: DNA
<213> ORGANISM: Aspergillus niger

<400> SEQUENCE: 1

```
atgggtgtct ctaatatgat gtcccggttc aagcctcagg cggaccactc tgagtcctcc     60
actgaggctc ctactcctgc tcgctccaac tccgccgtcg agaaggacaa tgtcttgctc    120
gatgacagtc ccgtcaagta cttgacctgg cgctccttca tcctgggtat cgtcgtgtcc    180
atgggtggtt tcatcttcgg ttactctact ggtcaaatct ctggtttcga gactatggat    240
gacttcctcc aacgtttcgg tcaggaacag gcggatggat cctatgcttt cagcaacgtc    300
cgtagtggtc tcattgtcgg tctgctgtgt atcggtacta tgatcggtgc cctggttgct    360
gctcctatcg cagaccgcat gggccgcaag ctctccatct gtctctggtc tgtcatccac    420
atcgtcggta tcatcattca gattgccacc gactccaact gggtccaggt cgctatgggt    480
cgttgggttg ccggtctggg tgttggtgcc ctctccagca ttgtccccat gtaccagagt    540
gaatctgctc ccgtcaggt ccgtggtgcc atggtcagtg ccttccagct gttcgttgcc    600
ttcggtatct tcatctccta catcatcaac ttcggtaccg agagaatcca gtcgactgct    660
tcctggcgta tcaccatggg cattggcttc gcctggccct tgattctggc tgttggctct    720
ctcttcctgc ccgagtctcc tcgtttcgcc taccgtcagg tcgtatcga tgaggcccgt    780 gaggttatgt gcaagctgta cggtgtcagc ccgaaccacc gcgtcatcgc ccaggagatg    840
aaggacatga aggacaagct cgacgaggag aaggccgccg gtcaggctgc ctggcacgag    900
ctgttcaccg gccctcgcat gctctaccgt accctgctcg gtattgctct gcagtccctc    960
cagcagctga ccggtgccaa cttatcttc tactacggaa acagtatctt cacctccact    1020
ggtctgagca acagctacgt cactcagatc attctgggtg ctgtcaactt cggtatgacc    1080
```

```
ctgcccggtc tgtacgtcgt cgagcacttc ggtcgtcgta acagtctgat ggttggtgct    1140
gcctggatgt tcatttgctt catgatctgg gcttccgttg gtcacttcgc tctggatctt    1200
gccgaccctc aggccactcc tgccgctggt aaggccatga tcatcttcac ttgcttcttc    1260
attgtcggtt tcgccaccac ctggggtcct atcgtctggg ccatctgtgg tgagatgtac    1320
cccgcccgct accgtgctct ctgcattggt attgccaccg ctgccaactg acctggaac    1380 ttcctcatct ccttcttcac ccccttcatc tctagctcca ttgacttcgc ctacggctac    1440
gtctttgctg gatgctgttt cgccgccatc ttcgttgtct tcttcttcgt caatgagacc    1500
cagggtcgca ctcttgagga ggttgacacc atgtacgtgc tccacgtcaa gccctggcag    1560
agtgccagct gggttccccc ggagggcatt gtccaggaca tgcaccgccc ccttcctct    1620 tccaagcagg agggtcaggc tgagatggct gagcacaccg agcccactga gctccgcgag    1680
taa                                                                  1683

<210> SEQ ID NO 2
<211> LENGTH: 560
<212> TYPE: PRT
<213> ORGANISM: Aspergillus niger

<400> SEQUENCE: 2

Met Gly Val Ser Asn Met Met Ser Arg Phe Lys Pro Gln Ala Asp His
 1               5                  10                  15

Ser Glu Ser Ser Thr Glu Ala Pro Thr Pro Ala Arg Ser Asn Ser Ala
                20                  25                  30

Val Glu Lys Asp Asn Val Leu Leu Asp Asp Ser Pro Val Lys Tyr Leu
            35                  40                  45

Thr Trp Arg Ser Phe Ile Leu Gly Ile Val Val Ser Met Gly Gly Phe
        50                  55                  60

Ile Phe Gly Tyr Ser Thr Gly Gln Ile Ser Gly Phe Glu Thr Met Asp
65                  70                  75                  80

Asp Phe Leu Gln Arg Phe Gly Gln Glu Gln Ala Asp Gly Ser Tyr Ala
                85                  90                  95

Phe Ser Asn Val Arg Ser Gly Leu Ile Val Gly Leu Leu Cys Ile Gly
            100                 105                 110

Thr Met Ile Gly Ala Leu Val Ala Ala Pro Ile Ala Asp Arg Met Gly
        115                 120                 125

Arg Lys Leu Ser Ile Cys Leu Trp Ser Val Ile His Ile Val Gly Ile
    130                 135                 140

Ile Ile Gln Ile Ala Thr Asp Ser Asn Trp Val Gln Val Ala Met Gly
145                 150                 155                 160

Arg Trp Val Ala Gly Leu Gly Val Gly Ala Leu Ser Ser Ile Val Pro
                165                 170                 175

Met Tyr Gln Ser Glu Ser Ala Pro Arg Gln Val Arg Gly Ala Met Val
            180                 185                 190

Ser Ala Phe Gln Leu Phe Val Ala Phe Gly Ile Phe Ile Ser Tyr Ile
        195                 200                 205

Ile Asn Phe Gly Thr Glu Arg Ile Gln Ser Thr Ala Ser Trp Arg Ile
    210                 215                 220

Thr Met Gly Ile Gly Phe Ala Trp Pro Leu Ile Leu Ala Val Gly Ser
225                 230                 235                 240

Leu Phe Leu Pro Glu Ser Pro Arg Phe Ala Tyr Arg Gln Gly Arg Ile
                245                 250                 255
```

```
Asp Glu Ala Arg Glu Val Met Cys Lys Leu Tyr Gly Val Ser Pro Asn
            260                 265                 270

His Arg Val Ile Ala Gln Glu Met Lys Asp Met Lys Asp Lys Leu Asp
        275                 280                 285

Glu Glu Lys Ala Ala Gly Gln Ala Ala Trp His Glu Leu Phe Thr Gly
    290                 295                 300

Pro Arg Met Leu Tyr Arg Thr Leu Leu Gly Ile Ala Leu Gln Ser Leu
305                 310                 315                 320

Gln Gln Leu Thr Gly Ala Asn Phe Ile Phe Tyr Gly Asn Ser Ile
                325                 330                 335

Phe Thr Ser Thr Gly Leu Ser Asn Ser Tyr Val Thr Gln Ile Ile Leu
            340                 345                 350

Gly Ala Val Asn Phe Gly Met Thr Leu Pro Gly Leu Tyr Val Val Glu
        355                 360                 365

His Phe Gly Arg Arg Asn Ser Leu Met Val Gly Ala Ala Trp Met Phe
    370                 375                 380

Ile Cys Phe Met Ile Trp Ala Ser Val Gly His Phe Ala Leu Asp Leu
385                 390                 395                 400

Ala Asp Pro Gln Ala Thr Pro Ala Ala Gly Lys Ala Met Ile Ile Phe
                405                 410                 415

Thr Cys Phe Phe Ile Val Gly Phe Ala Thr Thr Trp Gly Pro Ile Val
            420                 425                 430

Trp Ala Ile Cys Gly Glu Met Tyr Pro Ala Arg Tyr Arg Ala Leu Cys
        435                 440                 445

Ile Gly Ile Ala Thr Ala Ala Asn Trp Thr Trp Asn Phe Leu Ile Ser
450                 455                 460

Phe Phe Thr Pro Phe Ile Ser Ser Ser Ile Asp Phe Ala Tyr Gly Tyr
465                 470                 475                 480

Val Phe Ala Gly Cys Cys Phe Ala Ala Ile Phe Val Val Phe Phe Phe
                485                 490                 495

Val Asn Glu Thr Gln Gly Arg Thr Leu Glu Glu Val Asp Thr Met Tyr
            500                 505                 510

Val Leu His Val Lys Pro Trp Gln Ser Ala Ser Trp Val Pro Pro Glu
        515                 520                 525

Gly Ile Val Gln Asp Met His Arg Pro Pro Ser Ser Ser Lys Gln Glu
530                 535                 540

Gly Gln Ala Glu Met Ala Glu His Thr Glu Pro Thr Glu Leu Arg Glu
545                 550                 555                 560

<210> SEQ ID NO 3
<211> LENGTH: 1493
<212> TYPE: DNA
<213> ORGANISM: Aspergillus niger

<400> SEQUENCE: 3
ctgctctctc tctgctctct ttctgcgctc tctgtgtcgg cactaacccc gaatggggcg      60
ggtatcggca gtccgacgga tctccggggg ccgcacgtcc agcgccgatc gttactcaac     120
cgagcagagg agagagagca gtgagcagtg gtgtcaccga ccataaaaat gcttgcttct     180
gcccatccag ccatcagttg tccagtctgc tccattgtgt gccagtctcg ccccaaggc     240 cgcgcatctg aaaccaaccg gttgggtgaa atcagccggc gggtggcacc cgagcggcca     300
ctggctggga tcatcgcccg caacgcgtca acagcaatca aacgaaggat gcgaaattat     360
tcagcgggcg gttcctttcc aatttttccc cgttcctgtc agcatgtcta ctctatcata     420
```

-continued

| | |
|---|---|
| ctgtaacatt attatattgt gattatttt attctgggtg atgtgtccac tggaccgcac | 480 |
| gtggaatgaa gattttcctt ccctcgggac gagaaaccat ggcgcagttg gtgttgtgtg | 540 |
| cgtgtgtgtg cgtgtcggtt gtccgaaaat cgccctaaac tccgaggcac gcaccatttg | 600 |
| ccattaattc ccttgcgatt gatttctgcc tgtccctgcg acccttttgtg accctttgtg | 660 |
| acccttttgac cctggattca ggggcttggt ggactcatag cgatggggat agggacttt | 720 |
| gaccctttttg acccttttgac ctcccctttt tccctggcct aagtacgctg tagtcgtaat | 780 |
| tatagaaaga atcttgcgtg gactggggca aaagggaac agaacttatc catgtccgag | 840 |
| cagcgatcgg ccagtcacca agccggctgg atccgagacc cgctacgtgg gaactcccaa | 900 |
| gagtcgttaa gcaaagccaa gagatcagcc aagatgtcgc tcacgagcct aattgctgga | 960 |
| ttgccatatc gcttgtcgtt gtaccatcgc gtaagatttt atcattgttt ctggggctg | 1020 |
| tcagctagtc taaaacgtac tcctcaaacc agagaggctg atgatgctga tgatgggcct | 1080 |
| ccacccccca aattggtagc gccgttccat gagaggccca gtctctctct gcccgtcctc | 1140 |
| gaccattgtt tggcccagca ctgacacaac cttcaggggg ggccaatgga cgtattccgt | 1200 |
| aggcagcagg caaatgcggc cctaagaact ccccaactaa taagagtcca gactagcaaa | 1260 |
| ggttcgcctc gccggtctcc atctcttcct tcttagtcct cccatttcct ccctcccact | 1320 |
| tggtctctcg ctccagattt cctttcttct ttcatccatc ccatcttgta tccttttgct | 1380 |
| tagccttttt gtttggtttt cttcctctcg ttaaccacca cattcgctct atcttaatac | 1440 |
| aaaccaccca cactcgttct atagcatctg tcttctttcg ttcacctcct cac | 1493 |

<210> SEQ ID NO 4
<211> LENGTH: 2310
<212> TYPE: DNA
<213> ORGANISM: Artificial Sequence
<220> FEATURE:
<223> OTHER INFORMATION: Synthetic DNA

<400> SEQUENCE: 4

| | |
|---|---|
| caattccctt gtatctctac acacaggctc aaatcaataa gaagaacggt tcgtcttttt | 60 |
| cgttttatatc ttgcatcgtc ccaaagctat tggcgggata ttctgtttgc agttggctga | 120 |
| cttgaagtaa tctctgcaga tctttcgaca ctgaaatacg tcgagcctgc tccgcttgga | 180 |
| agcggcgagg agcctcgtcc tgtcacaact accaacatgg agtacgataa gggccagttc | 240 |
| cgccagctca ttaagagcca gttcatgggc gttggcatga tggccgtcat gcatctgtac | 300 |
| ttcaagtaca ccaaccctct tctgatccag tcgatcatcc cgctgaaggg cgcttttcgaa | 360 |
| tcgaatctgg ttaagatcca cgtcttcggg aagccagcga ctggtgaccct ccagcgtccc | 420 |
| tttaaggctg ccaacagctt tctcagccag ggccagccca agaccgacaa ggcctccctc | 480 |
| cagaacgccg agaagaactg gagggggtggt gtcaaggagg agtaagctcc ttattgaagt | 540 |
| cggaggacgg agcggtgtca agaggatatt cttcgctctg tattatagat aagatgatga | 600 |
| ggaattggag gtagcatagc ttcatttgga tttgcttttcc aggctgagac tctagcttgg | 660 |
| agcatagagg gtcccttttgg ctttcaatat tctcaagtat ctcgagtttg aacttattcc | 720 |
| cgtgaacctt ttattcacca atgagcattg gaatgaacat gaatctgagg actgcaatcg | 780 |
| ccatgaggtt ttcgaaatac atccggatgt cgaaggcttg gggcacctgc gttggttgaa | 840 |
| tttagaacgt ggcactattg atcatccgat agctctgcaa agggcgttgc acaatgcaag | 900 |
| tcaaacgttg ctagcagttc caggtggaat gttatgatga gcattgtatt aaatcaggag | 960 |
| atatagcatg atctctagtt agctcaccac aaaagtcaga cggcgtaacc aaaagtcaca | 1020 |

```
caacacaagc tgtaaggatt tcggcacggc tacggaagac ggagaagccc accttcagtg    1080
gactcgagta ccatttaatt ctatttgtgt ttgatcgaga cctaatacag cccctacaac    1140
gaccatcaaa gtcgtatagc taccagtgag gaagtggact caaatcgact tcagcaacat    1200
ctcctggata aactttaagc ctaaactata cagaataaga tggtggagag cttataccga    1260
gctcccaaat ctgtccagat catggttgac cggtgcctgg atcttcctat agaatcatcc    1320
ttattcgttg acctagctga ttctggagtg acccagaggg tcatgacttg agcctaaaat    1380
ccgccgcctc caccatttgt agaaaaatgt gacgaactcg tgagctctgt acagtgaccg    1440
gtgactcttt ctggcatgcg gagagacgga cggacgcaga gagaagggct gagtaataag    1500
cgccactgcg ccagacagct ctggcggctc tgaggtgcag tggatgatta ttaatccggg    1560
accggccgcc cctccgcccc gaagtggaaa ggctggtgtg cccctcgttg accaagaatc    1620
tattgcatca tcggagaata tggagcttca tcgaatcacc ggcagtaagc gaaggagaat    1680
gtgaagccag gggtgtatag ccgtcggcga aatagcatgc cattaaccta ggtacagaag    1740
tccaattgct tccgatctgg taaaagattc acgagatagt accttctccg aagtaggtag    1800
agcgagtacc cggcgcgtaa gctccctaat tggcccatcc ggcatctgta gggcgtccaa    1860
atatcgtgcc tctcctgctt tgcccggtgt atgaaaccgg aaaggccgct caggagctgg    1920
ccagcggcgc agaccgggaa cacaagctgg cagtcgaccc atccggtgct ctgcactcga    1980
cctgctgagg tccctcagtc cctggtaggc agctttgccc cgtctgtccg cccggtgtgt    2040
cggcggggtt gacaaggtcg ttgcgtcagt ccaacatttg ttgccatatt ttcctgctct    2100
ccccaccagc tgctctttc ttttctcttt cttttcccat cttcagtata ttcatcttcc    2160
catccaagaa cctttatttc ccctaagtaa gtactttgct acatccatac tccatccttc    2220 ccatcccta ttcctttgaa cctttcagtt cgagctttcc cacttcatcg cagcttgact    2280
aacagctacc ccgcttgagc agacatcacc                                   2310
```

<210> SEQ ID NO 5
<211> LENGTH: 1020
<212> TYPE: DNA
<213> ORGANISM: Artificial Sequence
<220> FEATURE:
<223> OTHER INFORMATION: Synthetic DNA

<400> SEQUENCE: 5

```
atgcctgaac tcaccgcgac gtctgtcgag aagtttctga tcgaaaagtt cgacagcgtc     60
tccgacctga tgcagctctc ggagggcgaa gaatctcgtg ctttcagctt cgatgtagga    120
gggcgtggat atgtcctgcg ggtaaatagc tgcgccgatg gtttctacaa agatcgttat    180
gtttatcggc actttgcatc ggccgcgctc ccgattccgg aagtgcttga cattgggaa     240 ttcagcgaga gcctgaccta ttgcatctcc cgccgtgcac agggtgtcac gttgcaagac    300
ctgcctgaaa ccgaactgcc cgctgttctg cagccggtcg cggaggccat ggatgcgatc    360
gctgcggccg atcttagcca gacgagcggg ttcggcccat tcggaccgca aggaatcggt    420
caatacacta catggcgtga tttcatatgc gcgattgctg atccccatgt gtatcactgg    480
caaactgtga tggacgacac cgtcagtgcg tccgtcgcgc aggctctcga tgagctgatg    540
ctttgggccg aggactgccc cgaagtccgg cacctcgtgc acgcggattt cggctccaac    600
aatgtcctga cggacaatgg ccgcataaca gcggtcattg actggagcga ggcgatgttc    660
ggggattccc aatacgaggt cgccaacatc ttcttctgga ggccgtggtt ggcttgtatg    720
```

```
gagcagcaga cgcgctactt cgagcggagg catccggagc ttgcaggatc gccgcggctc      780
cgggcgtata tgctccgcat tggtcttgac caactctatc agagcttggt tgacggcaat      840
ttcgatgatg cagcttgggc gcagggtcga tgcgacgcaa tcgtccgatc cggagccggg      900
actgtcgggc gtacacaaat cgcccgcaga agcgcggccg tctggaccga tggctgtgta      960
gaagtactcg ccgatagtgg aaaccgacgc cccagcactc gtccgagggc aaaggaatag     1020
```

<210> SEQ ID NO 6
<211> LENGTH: 771
<212> TYPE: DNA
<213> ORGANISM: Artificial Sequence
<220> FEATURE:
<223> OTHER INFORMATION: Synthetic DNA

<400> SEQUENCE: 6

```
gatccactta acgttactga aatcatcaaa cagcttgacg aatctggata taagatcgtt       60
ggtgtcgatg tcagctccgg agttgagaca aatggtgttc aggatctcga taagatacgt      120
tcatttgtcc aagcagcaaa gagtgccttc tagtgattta atagctccat gtcaacaaga      180
ataaaacgcg tttcgggttt acctcttcca gatacagctc atctgcaatg cattaatgca      240
ttggacctcg caaccctagt acgcccttca ggctccggcg aagcagaaga atagcttagc      300
agagtctatt ttcattttcg ggagacgaga tcaagcagat caacggtcgt caagagacct      360
acgagactga ggaatccgct cttggctcca cgcgactata tatttgtctc taattgtact      420
ttgacatgct cctcttcttt actctgatag cttgactatg aaaattccgt caccagcccc      480
tgggttcgca aagataattg cactgtttct tccttgaact ctcaagccta caggacacac      540
attcatcgta ggtataaacc tcgaaaatca ttcctactaa gatgggtata caatagtaac      600
catggttgcc tagtgaatgc tccgtaacac ccaatacgcc ggccgaaact tttttacaac      660
tctcctatga gtcgtttacc cagaatgcac aggtacactt gtttagaggt aatccttctt      720
tctagaagtc ctcgtgtact gtgtaagcgc ccactccaca tctccactcg a                771
```

<210> SEQ ID NO 7
<211> LENGTH: 31
<212> TYPE: DNA
<213> ORGANISM: Artificial Sequence
<220> FEATURE:
<223> OTHER INFORMATION: Synthetic DNA

<400> SEQUENCE: 7

```
ctgcaggatc cacttaaacg ttactgaaat c                                      31
```

<210> SEQ ID NO 8
<211> LENGTH: 28
<212> TYPE: DNA
<213> ORGANISM: Artificial Sequence
<220> FEATURE:
<223> OTHER INFORMATION: Synthetic DNA

<400> SEQUENCE: 8

```
aagcttctcg agtggagatg tggagtgg                                          28
```

<210> SEQ ID NO 9
<211> LENGTH: 30
<212> TYPE: DNA
<213> ORGANISM: Artificial Sequence
<220> FEATURE:
<223> OTHER INFORMATION: Synthetic DNA

<400> SEQUENCE: 9

```
<210> SEQ ID NO 10
<211> LENGTH: 30
<212> TYPE: DNA
<213> ORGANISM: Artificial Sequence
<220> FEATURE:
<223> OTHER INFORMATION: Synthetic DNA

<400> SEQUENCE: 10
ggtaccgtga ggaggtgaac gaaagaagac                                        30

<210> SEQ ID NO 11
<211> LENGTH: 43
<212> TYPE: DNA
<213> ORGANISM: Artificial Sequence
<220> FEATURE:
<223> OTHER INFORMATION: Synthetic DNA

<400> SEQUENCE: 11
gttcacctcc tcacggtacc atgggtgtct ctaatatgat gtc                          43

<210> SEQ ID NO 12
<211> LENGTH: 43
<212> TYPE: DNA
<213> ORGANISM: Artificial Sequence
<220> FEATURE:
<223> OTHER INFORMATION: Synthetic DNA

<400> SEQUENCE: 12
taacgtttaa gtggatcgga tccttactcg cggagctcag tgg                          43

<210> SEQ ID NO 13
<211> LENGTH: 26
<212> TYPE: DNA
<213> ORGANISM: Artificial Sequence
<220> FEATURE:
<223> OTHER INFORMATION: Synthetic DNA

<400> SEQUENCE: 13
caattccctt gtatctctac acacag                                             26

<210> SEQ ID NO 14
<211> LENGTH: 22
<212> TYPE: DNA
<213> ORGANISM: Artificial Sequence
<220> FEATURE:
<223> OTHER INFORMATION: Synthetic DNA

<400> SEQUENCE: 14
ctcgagtgga gatgtggagt gg                                                 22
```